United States Patent
Linden et al.

(10) Patent No.: US 7,732,484 B2
(45) Date of Patent: Jun. 8, 2010

(54) USE OF SELECTIVE ADENOSINE $A_1$ RECEPTOR ALLOSTERIC ENHANCERS TO MANIPULATE ANGIOGENESIS

(75) Inventors: Joel Linden, Charlottesville, VA (US); Amy L. Tucker, Charlottesville, VA (US); Richard Price, Charlottesville, VA (US); Rebecca Youkey, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 10/343,587

(22) PCT Filed: Aug. 1, 2001

(86) PCT No.: PCT/US01/24094

§ 371 (c)(1), (2), (4) Date: Jan. 31, 2003

(87) PCT Pub. No.: WO02/09701

PCT Pub. Date: Feb. 7, 2002

(65) Prior Publication Data

US 2003/0212082 A1 Nov. 13, 2003

Related U.S. Application Data

(60) Provisional application No. 60/222,355, filed on Aug. 1, 2000.

(51) Int. Cl.
*A61K 31/381* (2006.01)
*A61K 31/335* (2006.01)

(52) U.S. Cl. ........................ 514/447; 514/450

(58) Field of Classification Search ................ 514/447, 514/450, 263.4
See application file for complete search history.

(56) References Cited

U.S. PATENT DOCUMENTS

| | | | |
|---|---|---|---|
| 4,877,876 A | 10/1989 | Tsuji et al. | |
| 5,189,049 A | 2/1993 | Frehel et al. | |
| 5,256,398 A | 10/1993 | McAfee et al. | |
| 5,504,090 A | 4/1996 | Neely | |
| 5,733,916 A | 3/1998 | Neely | |
| 5,854,081 A | 12/1998 | Linden et al. | |
| 5,877,180 A | 3/1999 | Linden et al. | |
| 5,939,432 A * | 8/1999 | Baraldi | 514/301 |
| 6,060,481 A | 5/2000 | LaNoue et al. | |
| 6,117,445 A | 9/2000 | Neely | |
| 6,117,878 A | 9/2000 | Linden | |

(Continued)

FOREIGN PATENT DOCUMENTS

EP   0497258   8/1992

(Continued)

OTHER PUBLICATIONS

Xu et al., FASEB, 8(4-5) (1994), A79.*

(Continued)

*Primary Examiner*—Phyllis G. Spivack
(74) *Attorney, Agent, or Firm*—Kilpatrick Stockton LLP

(57) ABSTRACT

Disclosed is the use of selective adenosine $A_1$ allosteric enhancers to induce angiogenesis at a desired location for treating conditions in which increased angiogenesis is desired, such as stroke, heart disease and peripheral vascular disease.

18 Claims, 8 Drawing Sheets

U.S. PATENT DOCUMENTS

Figure 1:
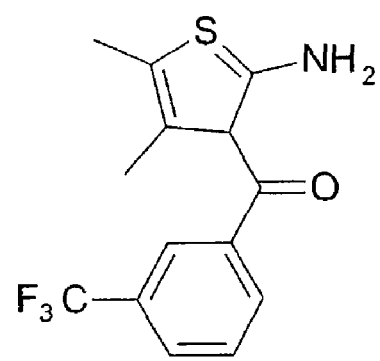

| | | | |
|---|---|---|---|
| 6,177,444 B1 | 1/2001 | Baraldi | |
| 6,232,297 B1 | 5/2001 | Linden et al. | |
| 6,251,922 B1 | 6/2001 | Jahne et al. | |
| 6,303,619 B1 | 10/2001 | Linden | |
| 6,440,947 B1 * | 8/2002 | Barron et al. | 514/46 |
| 6,448,235 B1 | 9/2002 | Linden et al. | |
| 6,476,059 B1 | 11/2002 | Jahne et al. | |
| 6,514,949 B1 | 2/2003 | Linden et al. | |
| 6,545,002 B1 | 4/2003 | Linden et al. | |
| 6,670,334 B2 | 12/2003 | Linden et al. | |
| 6,713,638 B2 * | 3/2004 | Linden et al. | 549/57 |
| 7,019,027 B2 | 3/2006 | Linden et al. | |
| 2002/0082240 A1 | 6/2002 | Linden et al. | |
| 2002/0111327 A1 | 8/2002 | Linden et al. | |
| 2003/0078248 A1 | 4/2003 | Linden et al. | |
| 2003/0186926 A1 | 10/2003 | Linden et al. | |
| 2003/0212082 A1 | 11/2003 | Linden et al. | |
| 2004/0180948 A1 | 9/2004 | Linden et al. | |
| 2005/0027125 A1 | 2/2005 | Linden et al. | |
| 2005/0182018 A1 | 8/2005 | Linden et al. | |
| 2005/0261236 A1 | 11/2005 | Okusa et al. | |
| 2006/0040888 A1 | 2/2006 | Rieger et al. | |
| 2006/0040889 A1 | 2/2006 | Rieger et al. | |
| 2006/0100169 A1 | 5/2006 | Rieger et al. | |

FOREIGN PATENT DOCUMENTS

| | | |
|---|---|---|
| EP | 0 503 563 A | 9/1992 |
| EP | 0970696 | 1/2000 |
| EP | 1 084 710 A | 3/2001 |
| WO | WO 98/06845 | 3/1996 |
| WO | WO 98/57651 | 12/1998 |
| WO | WO 99/21617 A | 5/1999 |
| WO | WO 99/24450 | 5/1999 |
| WO | WO 99/34803 | 7/1999 |
| WO | WO 99/38532 | 8/1999 |
| WO | WO 00/02596 | 1/2000 |
| WO | WO 01/10391 | 3/2000 |

OTHER PUBLICATIONS

Desseau et al., Circulation Research, 59(2), (Aug. 1986), pp. 163-169.*

D'Ancona, S. et al., Effect of Dipyridamola, 5'-(N-Ethyl)-carboxamidaodenosine and 1,3-Dipropyl-8-(2-amino-4-chlorophenyl)-xanthine on LOVO Cell Growth and Morphology, Anticancer Research, vol. 14, No. 1A, pp. 93-97, Jan. 1994.

Neely, et al. "A1 Adenosine Receptor Antagonists Block Ischemia-reperfusion Injury of the Heart" Circulation. 94(9)[suppl II]:II-376-II-380 (1996).

Neely et al. A1 adenosine "Receptor Antagonists Block Ischemia-reperfusion Injury of the lung." Am. J. Physiol. 268 (Lung Cell. Mol. Physiol. 12):L1036-L1046 (1995).

Database Medline on STN, (Columbus, OH, USA), No. 96223462, Martin P. et al. Characterization of 8-(N-methylispropyl)amino-N6-(5'-endohydroxy- endonobornyl)-9-methyladenine (WRC-0571), a highly potent and selective, non-xanthine antagonist of A1 adenosine receptors, abstract, J. Pharmacol. and Exp. Therap., Feb. 1996, 276 (2), 490-9.

Burckhartt, B. et al., "Acadesine Extends the Window of Protection Afforded by Ischaemic Preconditioning in Conscious Rabbits," Cardiovascular Research, vol. 29, No. 5, 1995, pp. 653-657.

Grant, M.B. et al., "Adenosine Receptor Activation Induces Vascular Endothelial Growth Factor in Human Retinal Endothelial Cells," Circulation Research, vol. 85, No. 8, 1999, pp. 699-706.

Halle, J.N. et al., "Enhancing Adenosine A1 Receptor Binding Reduces Hypoxiolschemic Brain Injury in Newborn Rats," Brain Research, vol. 759, No. 2, 1997, pp. 309-312.

Mizumura, T. et al., "PD 81,723, an Allosteric Enhancer of the A1 Adenosine Receptor, Lowers the Threshold for Ischemic Preconditioning in Dogs," Circulation Research, vol. 79, No. 3, 1996, pp. 415-423.

Picano, E. et al., "European Stroke Prevention Study-2 Results: Serendipitous Demonstration of Neuroprotection Induced by Endogenous Adenosine Accumulation?" Trends in Pharmacological Sciences, vol. 19, No. 1, 1998, pp. 14-16.

Adamis, A. P. et al., "Inhibition of Vascular Endothelial Growth Factor Prevents Retinal Ischemia-Associated Iris Neovascularization in a Nonhuman Primate," Arch. Ophthalmol., vol. 114, pp. 68-71, 1996.

Aguilar, J. S. et al., "Isolation and Characterization of an Avian $A_1$ Adenosine Receptor Gene and a Related cDNA Clone," Biochem. J., vol. 307, pp. 729-734, 1995.

Baumgartner, I. et al., "Constitutive Expression of phVEGF$_{165}$ after Intramuscular Gene Transfer Promotes Collateral Vessel Development in Patients with Critical Limb Ischemia," Circulation, vol. 97, No. 12, pp. 1114-1123, 1998.

Barnhill, R. L. et al., "Biochemical Modulation of Angiogenesis in the Chorioallantoic Membrane of the Chick Embryo," Journal of Investigative Dermatology, vol. 81, No. 6, pp. 485-488, 1983.

Belardinelli, L. et al., "The Cardiac Effects of Adenosine," Progress in Cardiovascular Diseases, vol. 21, No. 1, pp. 73-97, 1989.

Bruns, R. F. et al., "Allosteric Enhancement of Adenosine $A_1$ Receptor Binding and Function by 2-Amino-3-Benzoylthiophenes" Molecular Pharmacology, vol. 38, pp. 939-949, 1990.

Bruns, R. F. et al., "Structure-Activity Relationships for Enhancement of Adenosine $A_1$ Receptor Binding by 2-Amino-3-Benzoylthiophenes," Molecular Pharmacology, vol. 38, pp. 950-958, 1990.

Dusseau, J. W. et al., "Hypoxia-Induced Angiogenesis in Chick Chorioallantoic Membranes: A Role for Adenosine," Respiration Physiology, vol. 71, pp. 33-44, 1988.

Dusseau, J. W. et al., "Stimulation of Angiogenesis by Adenosine on the Chick Chorioallantoic Membrane," Circulation Research, vol. 59, pp. 163-170, 1986.

Fischer, S. et al., "Expression of Vascular Permeability Factor/Vascular Endothelial Growth Factor in Pig Cerebral Microvascular Endothelial Cells and its Upregulation by Adenosine," Molecular Brain Research, vol. 28, pp. 141-148, 1995.

Folkman, J. et al., "Angiogenesis," Journal of Biological Chemistry, vol. 267, No. 16, pp. 10931-10934, 1992.

Fredholm, B. B. et al., "International Union of Pharmacology. XXV. Nomenclature and Classification of Adenosine Receptors," Pharmacological Reviews, vol. 53, No. 4, pp. 527-552, 2001.

Grant, M. B. et al., "Adenosine Receptor Activation Induces Vascular Endothelial Growth Factor in Human Retinal Endothelial Cells," Circulation Research, vol. 85, pp. 699-706, 1999.

Grant, M. B. et al., "Adenosine Mediates Human Retinal Endothelial Cell (HREC) Chemotaxis, Capillary Tube Formation and Stimulatory Cell Signaling Cascades (abstract)," IOVS, vol. 40, No. 4, 3240-B98, 1999.

Hood, J. et al., "Protein Kinase G Mediates Vascular Endothelial Growth Factor-Induced Raf-1 Activation and Proliferation in Human Endothelial Cells," Journal of Biological Chemistry, vol. 273, No. 36, pp. 23504-23508, 1998.

Iliodromitis, E. K. et al., "The PKC Activator PMA Preconditions Rabbit Heart in the Presence of Adenosine Receptor Blockade: Is 5'-Nucleotidase Important?" J. Mol. Cell Cardiol., vol. 30, pp. 2201-2211, 1998.

Jonzon, B. et al., "Adenosine Receptor-Mediated Changes in Cyclic AMP Production and DNA Synthesis in Cultured Arterial Smooth Muscle Cells," Journal of Cellular Physiology, vol. 124, pp. 451-456, 1985.

Leitman, D. C. et al., "Forskolin, Phosphodiesterase Inhibitors, and Cyclic AMP Analogs Inhibit Proliferation of Cultured Bovine Aortic Endothelial Cells," Journal of Cellular Physiology, vol. 127, pp. 237-243, 1986.

Linden, J., "Cloned Adenosine $A_3$ Receptors: Pharmacological Properties, Species Differences and Receptor Functions," TiPS, vol. 15, pp. 298-306, 1994.

Meininger, C. J. et al., "Is Adenosine a Growth Factor for Endothelial Cells? (abstract)" FASEB Journal, vol. 2, pp. A1714, #8238, 1988.

Meininger, C. J. et al., "Adenosine and Hypoxia Stimulate Proliferation and Migration of Endothelial Cells," American Journal of Physiology, vol. 255, pp. H554-H562, Part 2, 1988.

Meininger, C. J. et al., "Mechanisms Leading to Adenosine-Stimulated Proliferation of Microvascular Endothelial Cells," American Journal of Physiology, vol. 258, pp. H198-H206, Part 2, 1990.

Mizumura, T. et al., "PD 81,723, An Allosteric Enhancer of the $A_1$ Adenosine Receptor, Lowers the Threshold for Ischemic Preconditioning in Dogs," Circulation Research, vol. 79, pp. 415-423, 1996; web page at http://circres.ahajournals.org/cgi/content/full/79/3/415, as available via the Internet and printed Jan. 31, 2006.

Paty, P. S. K. et al., "Role of Adenosine in Platelet-Mediated Reduction in Pulmonary Vascular Permeability," American Journal of Physiology, vol. 262, pp. H771-H777, Part 2, 1992.

Poucher, S. M. et al., "The In Vitro Pharmacology of ZM 241385, A Potent, Non-Xanthine, $A_{2a}$ Selective Adenosine Receptor Antagonist," British Journal of Pharmacology, vol. 115, pp. 1096-1102, 1995.

Risau, W. et al., "Vasculogenesis," Annu. Rev. Cell Dev. Biol., vol. 11, pp. 73-91, 1995.

Schiele, J. O. et al., "Characterization of the Adenosine Receptor in Microvascular Coronary Endothelial Cells," European Journal of Pharmacology Molecular Pharmacology Section, vol. 269, pp. 51-58, 1994.

Sexl, V. et al, "Stimulation of Human Umbilical Vein Endothelial Cell Proliferation by $A_2$-Adenosine and $\beta_2$—Adrenoceptors," British Journal of Pharmacology, vol. 114, pp. 1577-1586, 1995.

Southgate, K. et al., "Serum-Induced Proliferation of Rabbit Aortic Smooth Muscle Cells from the Contractile State is Inhibited by 8-Br-cAMP but not 8-Br-cGMP," Atherosclerosis, vol. 82, 113-123, 1990.

Stone, G. A. et al., "Species Differences in High-Affinity Adenosine $A_2$ Binding Sites in Striatal Membranes from Mammalian Brain," Drug Development Research, vol. 15, pp. 31-46, 1988.

Sullivan, G. W. et al., "Rote of $A_{2A}$ Adenosine Receptors in Inflammation," Drug Development Research, vol. 45, pp. 103-112, 1998.

Takagi, H. et al., "Adenosine Mediates Hypoxic Induction of Vascular Endothelial Growth Factor in Retinal Pericytes and Endothelial Cells," Investigative Ophthalmology and Visual Science, vol. 37, No. 11, pp. 2165-2176, 1996.

Varani, K. et al., "Binding Affinity of Adenosine Receptor Agonists and Antagonists at Human Cloned $A_3$ Adenosine Receptors," Life Sciences, vol. 63, No. 5, pp. 81-87, 1998.

Van Calker, D. et al., "Carbamazepine Distinguishes between Adenosine Receptors that Mediate Different Second Messenger Responses," European Journal of Pharmacology Molecular Pharmacology Section, vol. 206, pp. 285-290, 1991.

Baraldi P.G. et al., "Synthesis of 2-amino-3-heteroaroylthiophenes and evaluation of their activity as potential allosteric enhancers at the human $A_1$ receptor," European Journal of Medical Chemistry, 39(2004):855-865.

Childers, S.R. et al., "Allosteric modulation of adenosine $A_1$ receptor coupling to G-proteins in brain," Journal of Neurochemistry, 93(2005):715-723.

Dusseau, J.W. et al., "Stimulation of angiogenesis by adenosine on the chick chorioallantoic membrane," Circulation Research, 59(1986):163-170.

Goblyos, A. et al., "Synthesis and biological evaluation of a new series of 2,3,5-substituted [1,2,4]-thiadiazoles as modulators of adenosine $A_1$ receptors and their molecular mechanism of action," J. Med. Chem., 48(2005):1145-1151.

Harris-Hooker, S.A. et al., "Neovascular responses induced by cultured aortic endothelial cells," Journal of Cellular Physiology, 114(1983):302-310.

Chordia, M. et al., 2-Aminothiazoles: A New Class of Agonist Allosteric Enhancers of $A_1$ Adenosine Receptors, Bioorganic & Medicinal Chemistry Letters, vol. 12, pp. 1563-1566, 2002.

Figler, H. et al., Allosteric Enhancers of $A_1$ Adenosine Receptors Increase Receptor-G Protein Coupling and Counteract Guanine Nucleotide Effects on Agonist Binding, Molecular Pharmacology, vol. 64, pp. 1557-1564, 2003.

Hutchinson, S. et al., New Potent and Selective $A_1$ Adenosine Receptor Agonists, Bioorganic & Medicinal Chemistry, vol. 12, pp. 4877-4884, 2004.

Kawata, H. et al., Ischemic Preconditioning Upregulates Vascular Endothelial Growth Factor mRNA Expression and Neovascularization via Nuclear Translocation of Protein Kinase C in the Rat Ischemic Myocardium, Circulation Research, vol. 88, 2001, web page at http://circres.ahajournals.org/cgi/content/full/88/7/696, as available via the Internet and printed May 12, 2008.

Nikolakopoulos, G. et al., 2-Aminothiophene-3-Carboxylates and Carboxamides as Adenosine $A_1$ Receptor Allosteric Enhancers, Bioorganic & Medicinal Chemistry, pp. 1-8, 2005 (article in press).

Olah, M. et al., I-4-Aminobenzyl-5'-N-Methylcarboxamidoadenosine, a High Affinity Radioligand for the Rat $A_3$. Adensoine Receptor, Molecular Pharmacology, vol. 45, pp. 978-982, 1994.

Schrader, J. et al., Coronary and Myocardial Adenosine Receptors, Biomed. Biochim. Acta, vol. 46, No. 8/9, pp. S421-S426, 1987.

Tranberg, C. et al., "2-Amino-3-aroyl-4,5-alkylthiophenes: Agonist Allosteric Enhancers at Human $A_1$ Adenosine Receptors," J. Med. Chem., vol. 45, 382-389, 2002.

Chemical Abstract, vol. 117, No. 11, Sep. 14, 1992 (Columbus, OH, USA) p. 857, col. 1, the abstract No. 111516b.

Chordia et al., "2-Aminothiazoles: A new Class of Agonist Allosteric Enhancers of A1 Adenosine Receptors," Bioorganic & Med. Chemistry Let., 2002, 12: 1563-1566.

Esses-Reiter et al., "Synthesis of C-nor-heterocyclic Steroid Analogs," J. Heterocyclic Chem., 1996, 33(3): 879-884.

Gupta et al., "Synthesis and Anti-inflammatory Activity of Some Substituted 2-amino-8H-indeno [1,2-d]thiazoles," Indian Journal of Pharmaceutical Sciences, 1991, 245-248.

Tinney et al., "Synthesis and Pharmaceutical Evaluation of 2,3-Dihydro-IH-Thieno [2,3-e][1,4] Diazepines," CA81:145630, 1974, (Abstract).

Amoah-Apraku, B. et al., "Selective Potentiation by an $A_1$ Adenosine Receptor Enhancer of the Negative Dromotropic Action of Adenosine in the Guinea Pig Heart," JPET, 1993, 266: 611-617.

Kollias-Baker, C. et al., "Allosteric Enhancer PD 81,723 Acts by Novel Mechanism to Potentiate Cardiac Actions of Adenosine," Circ. Res., 1994, 75; 961-971.

Kollias-Baker, C. et al., "Agonist-Independent Effect of an Allosteric Enhancer of the $A_1$ Adenosine Receptor in CHO Cells Stably Expressing the Recombinant Human $A_1$ Receptor," JPET, 1997, 281: 761-768.

Rankin, A. et al., "Adenosine and the Treatment of Supraventricular Tachycardia," Am. J. Med., 1992, 92: 655-664.

* cited by examiner

USE OF SELECTIVE ADENOSINE $A_1$ RECEPTOR ALLOSTERIC ENHANCERS TO MANIPULATE ANGIOGENESIS

CROSS-REFERENCE TO RELATED APPLICATION

This application claims priority of U.S. provisional patent application Ser. No. 60/222,355, filed Aug. 1, 2000.

TECHNICAL FIELD

The instant invention relates generally to methods of manipulating angiogenesis and more specifically it relates to the use of compounds which are selective adenosine $A_1$ receptor agonists, antagonists and allosteric enhancers to manipulate angiogenesis in animal subjects. These compounds, and compositions containing them, are useful for treating conditions in which angiogenesis is implicated.

DISCLOSURE OF THE INVENTION

Angiogenesis is the process whereby new vessels are formed from previously formed ones, and is a complex process involving a coordinated interaction between numerous cell types. The critical cells are the endothelial cells which contain all of the genetic information necessary to form primitive tubes and branches. Other cells, such as smooth muscle cells, mast cells, and macrophages release important modulators of angiogenesis. Hypoxia, decreased blood flow, and released angiogenic substances such as vascular endothelial growth factor (VEGF) can trigger angiogenesis. Angiogenesis is initiated by a breakdown in the extracellular matrix followed by proliferation and migration of endothelial cells into the tissue. The endothelial cells form cords initially, but later large vacuoles form in the cells leading to the formation of tubes. The endothelial tubes have a lumen, but are abnormally permeable and leaky until pericytes are recruited to reinforce the new vessels. Several growth factors, most notably VEGF, bFGF, and angiopoetin-1 have been demonstrated to promote angiogenesis. VEGF, a specific mitogen for endothelial cells, can independently stimulate new vessel growth. However, overexpression of VEGF in developing avian embryos results in large diameter vessels that are leak and lead to tissue edema. The coordinated effects of several growth factors may be necessary in order to stimulate development of normal new vasculature. Hence, finding ways to use upstream modulators in a tissue-specific way may provide a therapeutic advantage over the application of individual angiogenic growth factors.

Previous studies suggest that adenosine is released from hypoxic or ischemic tissue and that adenosine stimulates angiogenesis. Possible mechanisms include increased flow, stimulation of vascular cell proliferation and migration, or stimulation of angiogenic growth factor secretion. Some of the results obtained in previous studies on adenosine effects in vivo and in vitro have suggested that activation of adenosine $A_2$ receptors ($A_{2A}$ or $A_{2B}$) are responsible for the ability of adenosine to stimulate angiogenesis. The activation of $A_{2B}$ receptors on cultured endothelial cells has been shown to stimulate VEGF release. Most previous studies show a role for the $A_{2A}$ or $A_{2B}$ receptors, but little or no role for $A_1$ adenosine receptor activation in stimulating angiogenesis. The present invention is based on the data showing that the $A_1$ receptor is more important than has been previously thought. This is clinically significant because of the availability of allosteric enhancer compounds that selectively increase the functional effects of endogenous adenosine or adenosine agonists at $A_1$ receptors and because of the availability of selective $A_1$ antagonists to block angiogenesis. Allosteric enhancers of $A_1$ adenosine receptors are predicted to selectively stimulate angiogenesis in ischemic tissue and not in tissue that has adequate blood flow. This site-specificity represents a major advantage over other angiogeneic agents that are not selective for ischemic tissue.

There are widespread clinical applications for the manipulation of the angiogenic process in cardiovascular medicine, ophthalmology and oncology. Stimulating new vasculature in ischemic tissues, especially heart and limbs, could have a major impact on morbidity and mortality from atherosclerotic disease and is currently an active clinical endeavor. Trials in humans have shown the usefulness of VEGF in stimulating collateralization to ischemic lower extremities, resulting in improved ulcer healing and decreased limb loss. There are also ongoing clinical trials using VEGF infusions in patients with intractable, inoperable angina.

VEGF is a direct, or primary, angiogenic factor, meaning that it is able independently to induce angiogenesis in endothelial cells in vitro or in vivo. Secondary, or indirect, angiogenic factors work by causing cells to release primary factors. There is apprehension among scientists and clinicians about using primary factors clinically for fear that there will be pathologic angiogenesis in other tissues. Thus a limitation of using adenosine or other promoters of angiogenesis is the development of neovascularization in healthy as well as diseased tissues. Inhibition of angiogenesis to curtail tumor growth is as important a quest in oncology as stimulating it is in cardiovascular medicine, so the prospect of abnormal vessel stimulation is a real concern. Additionally, while VEGF is sufficient to stimulate the formation of new blood vessels, there is evidence that the growth of normal healthy vessels may require a coordinated action among several different growth factors. Hence, activation of upstream secondary angiogenic stimuli may produce a more regulated and normal vascular response. Additionally, the ability to target angiogenic stimulation to specific tissues would diminish the risk of undesirable systemic angiogenesis.

Adenosine has been shown to trigger angiogenesis in animal models and endothelial cell proliferation in cultured cells. Adenosine as a modulator of angiogenesis can be studied using the chicken chorioallantoic membrane (CAM) model. In addition, hypoxia initiates proliferation of cultured endothelial cells, a response that can be blocked by nonselective adenosine receptor antagonists. Hypoxia has long been considered a driving force for new blood vessel formation. Increased vascular density is seen in humans at high altitudes, in chronically stimulated skeletal muscle, and in rapidly growing tumors. In the CAM model, lowering oxygen concentration stimulates neovascularization. Adenosine is a logical modulator for the hypoxic stimulation of angiogenesis. It is a metabolite of ATP breakdown released from all ischemic or hypoxic tissues where it acts as a "retaliatory metabolite" to help restore normal oxygen delivery, initially by dilating existing blood vessels. Xanthine blockers of adenosine receptors have been shown to block the effects of hypoxia to stimulate endothelial cell proliferation. Adenosine has inconsistently been shown to be angiogenic in the chicken chorioallantoic membrane (CAM) model. Receptor subtype selective ligands have not previously been tested in the CAM. Subtype selective ligands have been employed to tease out the mechanism of adenosine-induced endothelial cell proliferation and migration, but the results have been inconsistent.

Adenosine acts via cell surface G protein coupled receptors of four known subtypes, $A_1$, $A_{2A}$, $A_{2B}$ and $A_3$. $A_1$ and $A_3$ receptors are the most similar in amino acid sequence and pharmacology. The $A_1$ and $A_3$ receptors couple to G proteins from the Gi/Go family that are pertussis toxin sensitive and inhibit adenylyl cyclase. Stimulation of $A_1$ and $A_3$ receptors can also activate phospholipase C, presumably via G protein βγ subunits. $A_{2A}$ and $A_{2B}$ receptors couple to Gs and stimulate adenylyl cyclase, but the $A_{2B}$ receptor can also couple to Gq, which is insensitive to pertussis toxin. In the heart, $A_1$ receptors have negative chronotropic, dromotropic and inotropic effects. The $A_1$ receptor, and perhaps the $A_3$, is also involved in the preconditioning phenomenon which protects ischemic myocardium. $A_{2A}$ receptors are expressed on coronary arteries and activation results in coronary vasodilation. $A_{2A}$ receptors are also found on leukocytes where they act to attenuate the inflammatory response and hence may decrease reperfusion injury. Accordingly, adenosine acts in a number of ways to protect ischemic tissues; it decreases metabolism, increases blood flow, and attenuates inflammatory injury. Adenosine activates $A_{2B}$ receptors on cultured endothelial cells to trigger VEGF release and endothelial mitogenesis. Adenosine also appears to stimulate angiogenesis, but to date no attempt has been made to define the adenosine receptor subtypes involved in the CAM model. Additionally, until the present invention it had not been shown that adenosine stimulates angiogenesis in adult mammalian models. The new development of more selective adenosine receptor ligands and cloning of the chicken $A_1$, $A_{2A}$, and $A_3$ receptors has enabled us to identify adenosine receptor subtypes participating in the CAM angiogenic response to adenosine.

Adenosine receptors are activated by modified analogues of adenosine and inhibited by xanthines, such as caffeine and other alkylxanthines. Recently non-xanthine antagonists have been described as well. The pharmacology of a given adenosine receptor subtype can vary widely among species. This is particularly true for the $A_1$ and $A_3$ receptors. The $A_1$ and $A_3$ receptors differ most among species in the binding of xanthine antagonists. $A_{2A}$ receptors show less variation in binding among species. The $A_{2B}$ receptor is a low affinity receptor for which there were no selective ligands until recently. While not extensively characterized, the recombinant chicken $A_1$ receptor shows a rank order potency for adenosine agonist ligands that is similar to that of rat and human $A_1$ receptors.

Cyclopentyladenosine (CPA) has long been known as a highly selective $A_1$ agonist, while the newly described non-xanthine $A_1$ antagonist WRC-0571 offers increased $A_1$ selectivity, especially between $A_1$ and $A_3$ receptors. CGS21680 is a potent and highly selective $A_{2A}$ agonist for all species studied to date; however, until recently, there were no stable, highly selective $A_{2A}$ antagonists. Now, several new highly selective $A_{2A}$ antagonist compounds are available, including ZM-241385, which block $A_{2A}$ receptors much more potently than $A_1$ receptors. The first $A_3$ receptor selective ligands have been recently described, and include the agonist $N^6$-iodobenzyl-5'-N-methyl-carboxamidoadenosine IB-MECA and the antagonist MRS 1191. MRS 1191 offers >1300-fold selectivity for the human $A_3$ over the $A_1$ receptor. Table 1 shows the ligands we have used to characterize the angiogenic response seen in the CAM.

TABLE 1

|  | $A_1$ | $A_{2A}$ | $A_{2B}$ | $A_3$ |
|---|---|---|---|---|
| Agonist | CPA | CGS21680 | NECA | IB-MECA |
| Antagonist | WRC-0571 | ZM-241385 | Enprofylline | MRS 1191 |

As discussed above, endothelial cells have all four subtypes of adenosine receptors, $A_1$, $A_{2A}$, $A_{2B}$ and $A_3$. Microvascular endothelial cells in culture proliferate and migrate in response to adenosine, but there is controversy surrounding which receptor subtype is responsible, especially for the proliferative response. The concentrations of agonists used in several of the previous investigations were too high to be subtype selective. Reports differ with respect to whether an increase in cAMP inhibits or stimulates a proliferative endothelial cell response. Several investigators report that the proliferative response is a result of $A_2$ receptor stimulation, however, it is pertussis sensitive, suggesting that it may result from $A_1$ or $A_3$ stimulation. Nitric oxide stimulates proliferation and migration of endothelial cells and adenosine upregulates endothelial cell nitric oxide synthase via an $A_2$ mechanism. Adenosine also upregulates VEGF mRNA and protein expression in several cell types, some via $A_2$ receptors, probably $A_{2A}$, and some via $A_1$. Finally, adenosine agonists stimulate proliferation of smooth muscle cells associated with a decrease in cAMP—suggesting that it is $A_1$ or $A_3$ mediated.

Several different adenosine receptor subtypes may be involved in coordinating angiogenesis, but our data obtained from the CAM assay during development of the current invention unexpectedly point to a major role for the adenosine $A_1$ receptor. We have discovered that stimulation of adenosine $A_1$ receptors with either selective $A_1$ agonists or allosteric enhancers selective for $A_1$ receptors elicits an angiogenic response in the CAM model.

Allosteric enhancers of receptors are defined as compounds that potentiate responses to agonists and bind to an allosteric site distinct from the binding site of the endogenous ligand. Benzodiazepines are allosteric enhancers of $GABA_A$ receptors. There are a number of other receptors for which allosteric enhancers or inhibitors have been described, including the muscarinic receptors and atrial natriuretic receptors. Allosteric enhancers of adenosine $A_1$ receptors are compounds that have little effect by themselves, but enhance the $A_1$ effects of endogenous adenosine in ischemic tissues.

PD 81,723 (PD) is one member of a family of aminothiophene compounds that were the first described allosteric enhancers of adenosine $A_1$ receptors. These compounds increase binding of [$^3$H]$N^6$-cyclohexyladenosine (CHA) to adenosine $A_1$ receptors and caused a functional enhancement of the effects of adenosine $A_1$ receptor activation in various tissues. PD is selective for adenosine $A_1$ receptors, having no effects on receptors of other classes or on other adenosine receptor subtypes. PD has shown enhancement at $A_1$ receptors from all species tested to date. In the absence of adenosine or $A_1$-selective agonists, the enhancer molecules alone act as very weak antagonists for adenosine receptors. The ability of allosteric enhancers, such as PD 81,723, to promote angiogenesis in two animal model systems, a chicken chorioallantoic membrane model and a rat mesenteric model has been tested. The data of the present invention show that the allosteric enhancer PD 81,723 stimulates angiogenesis in the CAM assay, as does the related compound C17. These data, along with data from $A_1$ selective agonists indicate that the $A_1$ receptor plays an important role in angiogenesis that was previously unknown. The reason that this is clinically important is because allosteric enhancers would theoretically work best in hypoxic tissues with high endogenous levels of adenosine, sparing other tissues from angiogenic effects where they are not needed.

Promoting angiogenesis is beneficial for revascularization of ischemic tissues in conditions such as stroke, heart disease, and peripheral vascular disease. Methods for treating stroke, heart disease, and peripheral vascular disease can thus effectively employ the administration a compound which promotes angiogenesis. The ability of allosteric enhancers, such as PD 81,723, to promote angiogenesis in two animal model systems, the chicken chorioallantoic membrane model and the rat mesenteric model, indicates that allosteric enhancers of the adenosine $A_1$ receptor enhance the ability of adenosine to promote angiogenesis.

Furthermore, it can be readily appreciated that selective adenosine $A_1$ receptor blockers can be used to inhibit angiogenesis in circumstances where angiogenesis contributes to a pathological condition. Pathologic angiogenesis plays a prominent role in conditions such as tumors, diabetic retinopathy, and in inflammatory diseases such as rheumatoid arthritis and psoriasis. Selective adenosine $A_1$ receptor blockers, such as WRC-0571, can block the angiogenic response to adenosine agonists and enhancers, and inhibit the angiogenic response to below control levels, suggesting that they can be used as inhibitors of angiogenesis.

Allosteric enhancers of adenosine $A_1$ receptors, such as PD 81,723, can be used therapeutically in patients with ischemic diseases to selectively stimulate angiogenesis in diseased tissues. Ischemic diseases include, but are not limited to angina, myocardial infarction, stroke, peripheral vascular disease, and infertility.

Selective adenosine $A_1$ receptor blockers, such as WRC-0571, can be used to inhibit angiogenesis. Conditions in which this will be useful include, but are not limited to, tumors, diabetic retinopathy, inflammatory diseases such as rheumatoid arthritis and psoriasis, and contraception.

Accordingly, the present invention provides a method of manipulating angiogenesis in a mammalian subject, such as a human, via the administration of a compound which acts as a selective adenosine $A_1$ receptor agonist, antagonist or allosteric enhancer. Administration of selective adenosine $A_1$ receptor agonists and/or allosteric enhancers acts to increase angiogenesis, while administration of selective adenosine $A_1$ receptor antagonists inhibit angiogenesis.

The invention also includes the use of such selective adenosine $A_1$ receptor agonists, antagonists or allosteric enhancers in the manufacture of medicaments for the treatment of a condition or symptom in a mammalian subject, such as a human, which is associated with angiogenesis.

The invention also includes the use of a combination of an adenosine $A_1$ allosteric enhancer with an adenosine $A_1$ agonist for synergistic stimulation of angiogenesis in a mammalian subject, such as a human.

Additionally, the invention provides a therapeutic method for preventing or treating a pathological condition or symptom in a mammal subject, such as a human, wherein increased angiogenesis is desired, comprising administering to a mammal in need of such therapy an effective amount of a selective adenosine $A_1$ agonist, allosteric enhancer, or combination of the two.

The invention also provides a therapeutic method for preventing or treating a pathological condition or symptom in a mammal subject, such as a human, wherein decreased angiogenesis is desired, comprising administering to a mammal in need of such therapy an effective amount of a selective adenosine $A_1$ antagonist.

BRIEF DESCRIPTION OF THE DRAWING FIGURES

Various other objects, features and attendant advantages of the present invention will become more fully appreciated as the same becomes better understood when considered in conjunction with the accompanying drawings.

Figure 2:
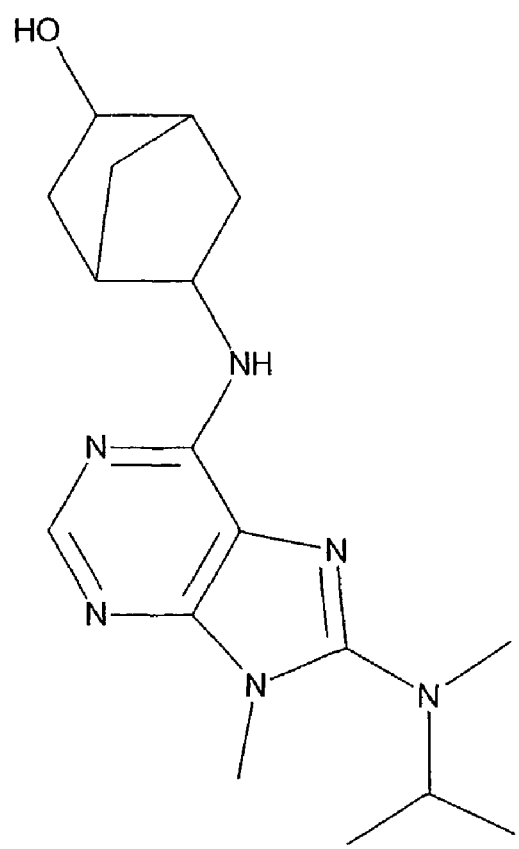
Figure 3:
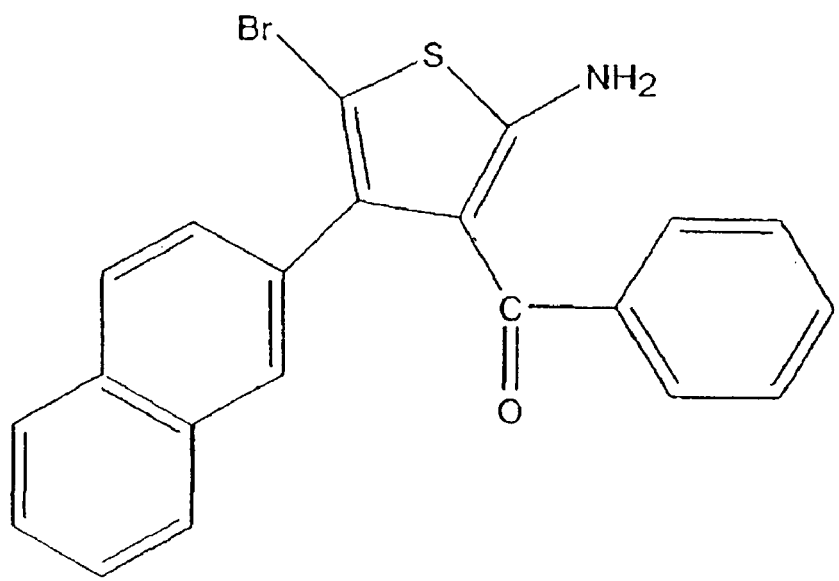
Figure 4:
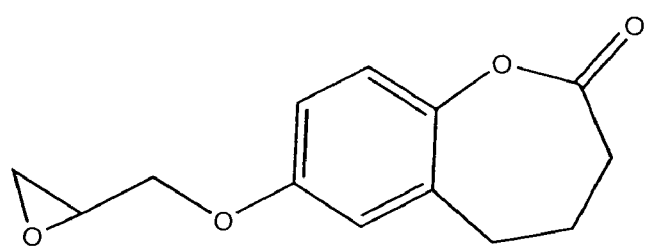
Figure 5:
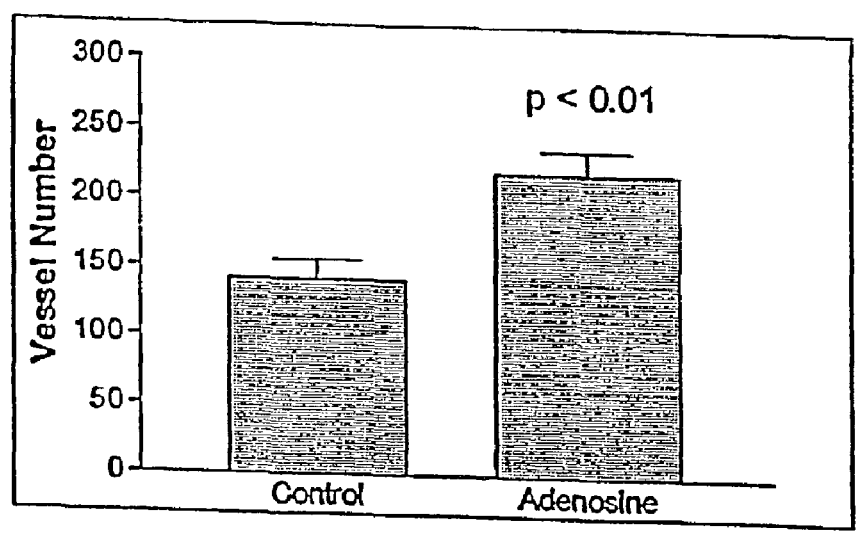
Figure 6:
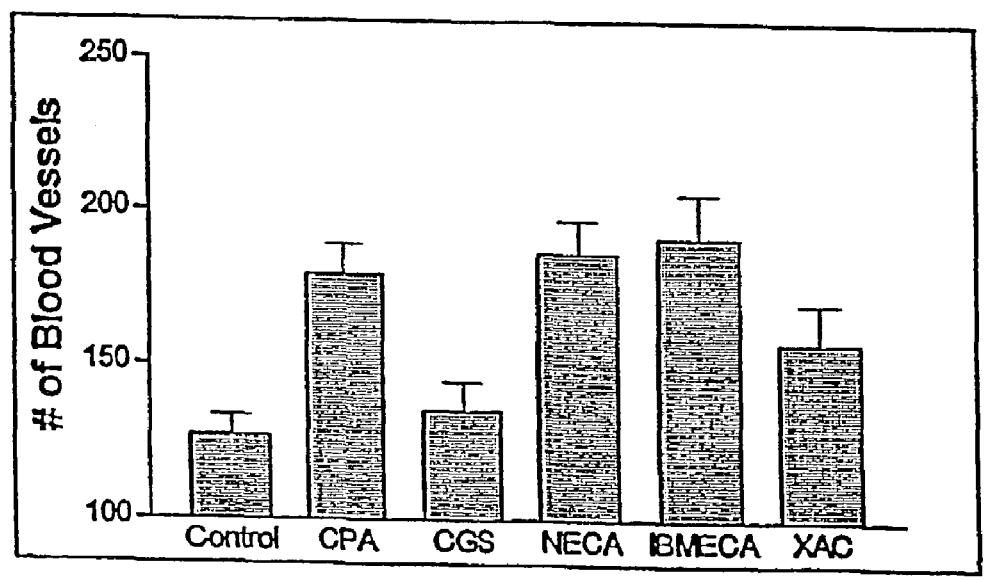
Figure 7:
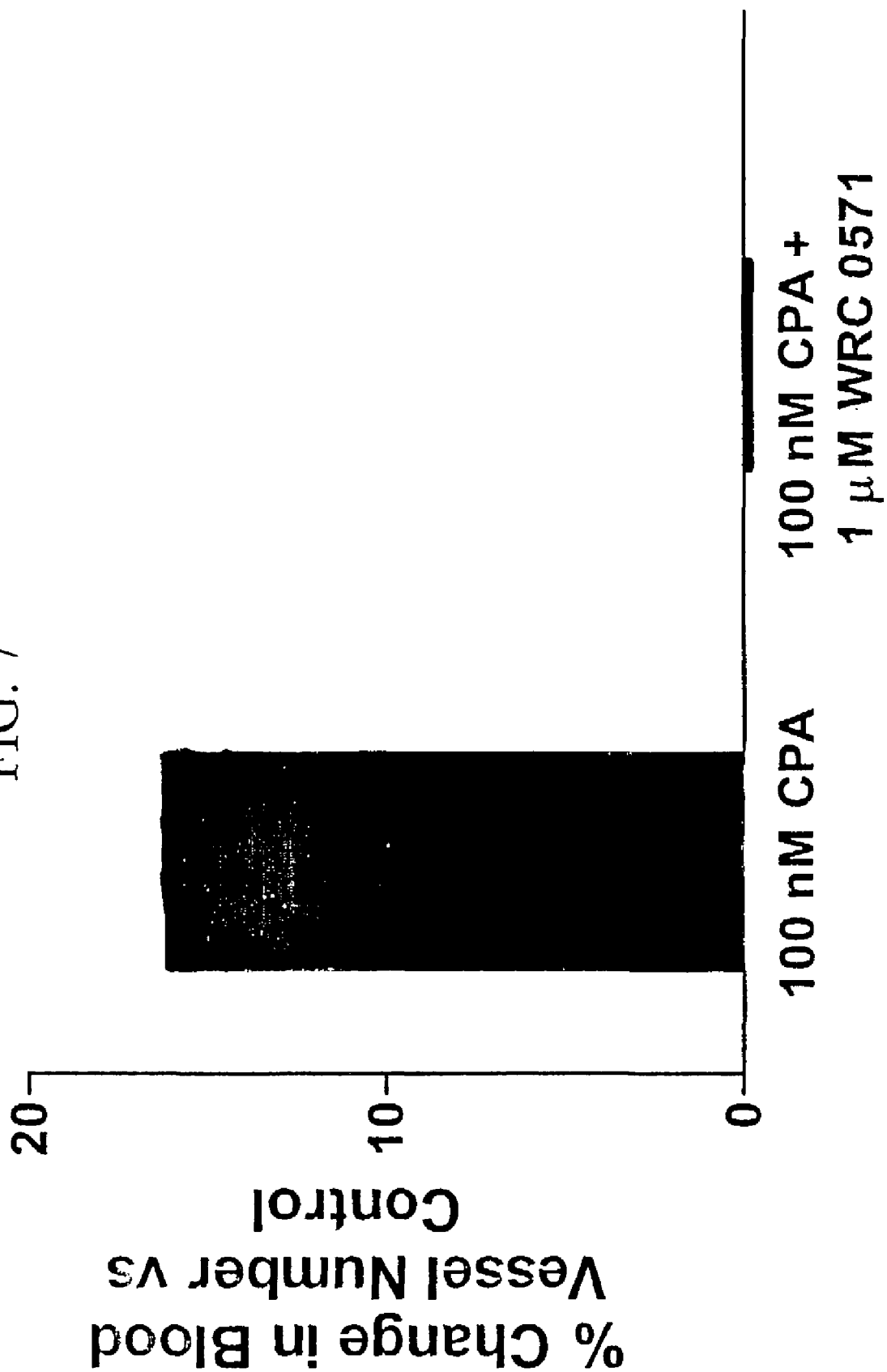
Figure 8:
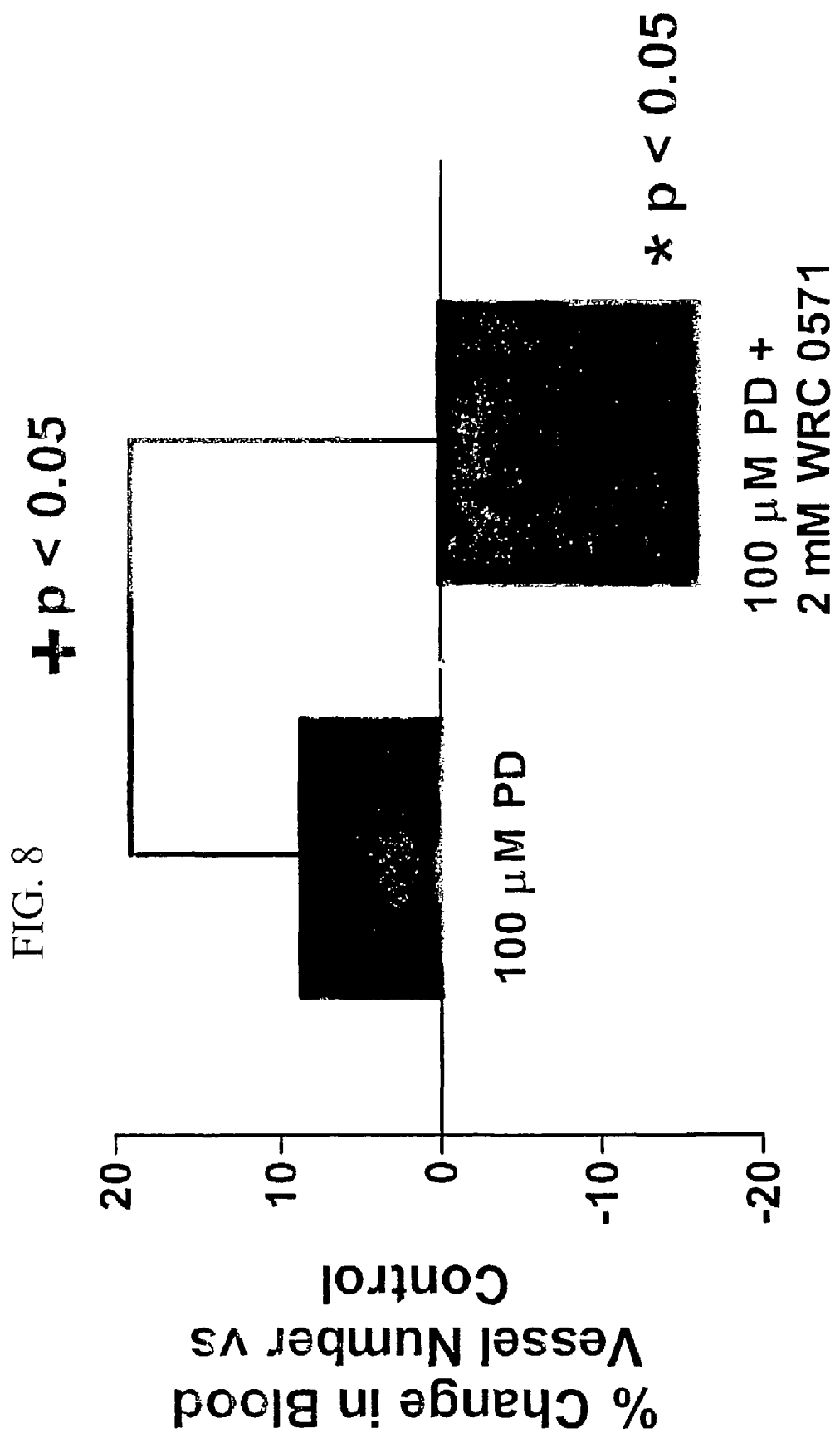
Figure 9:
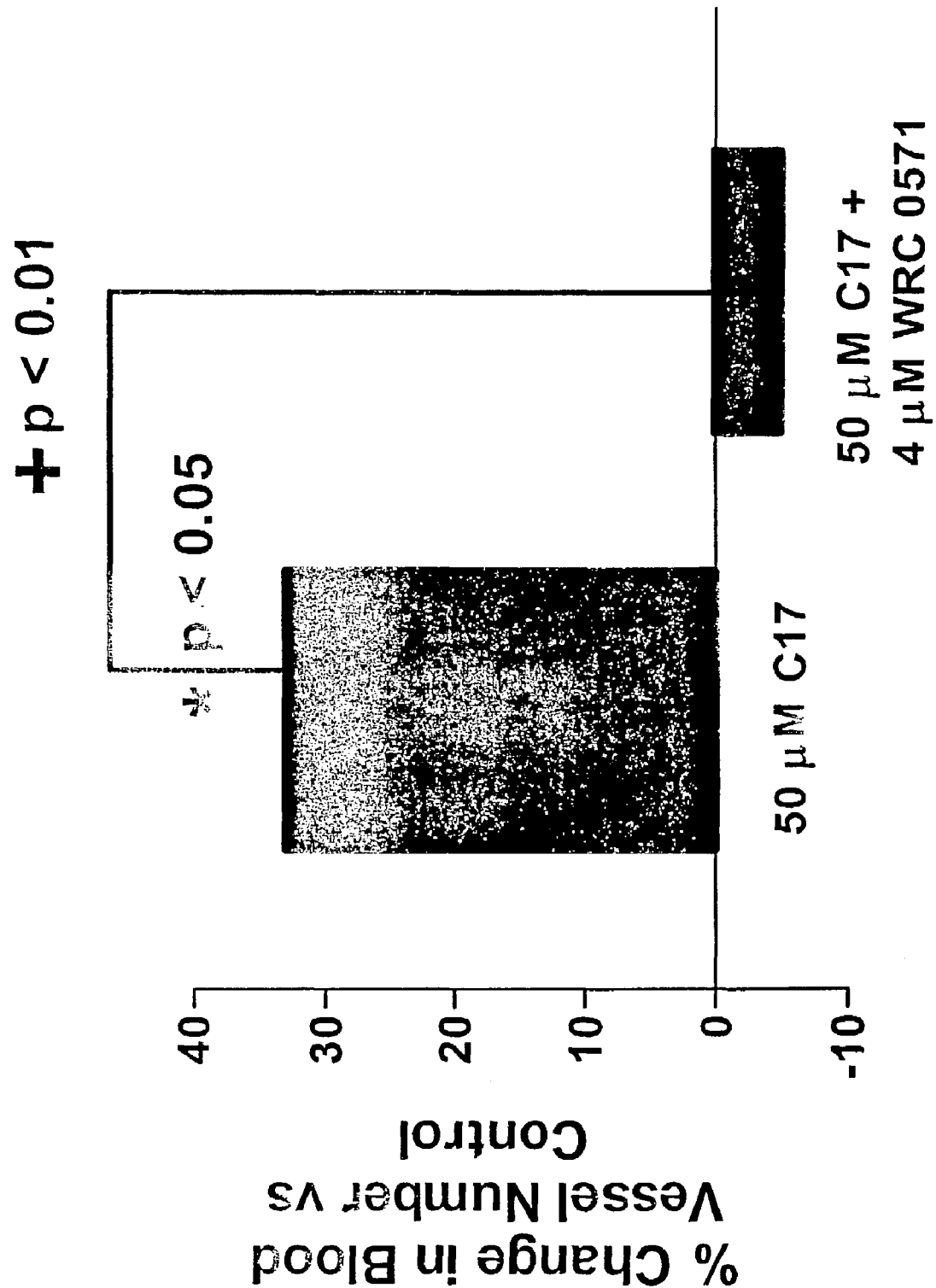
Figure 10:
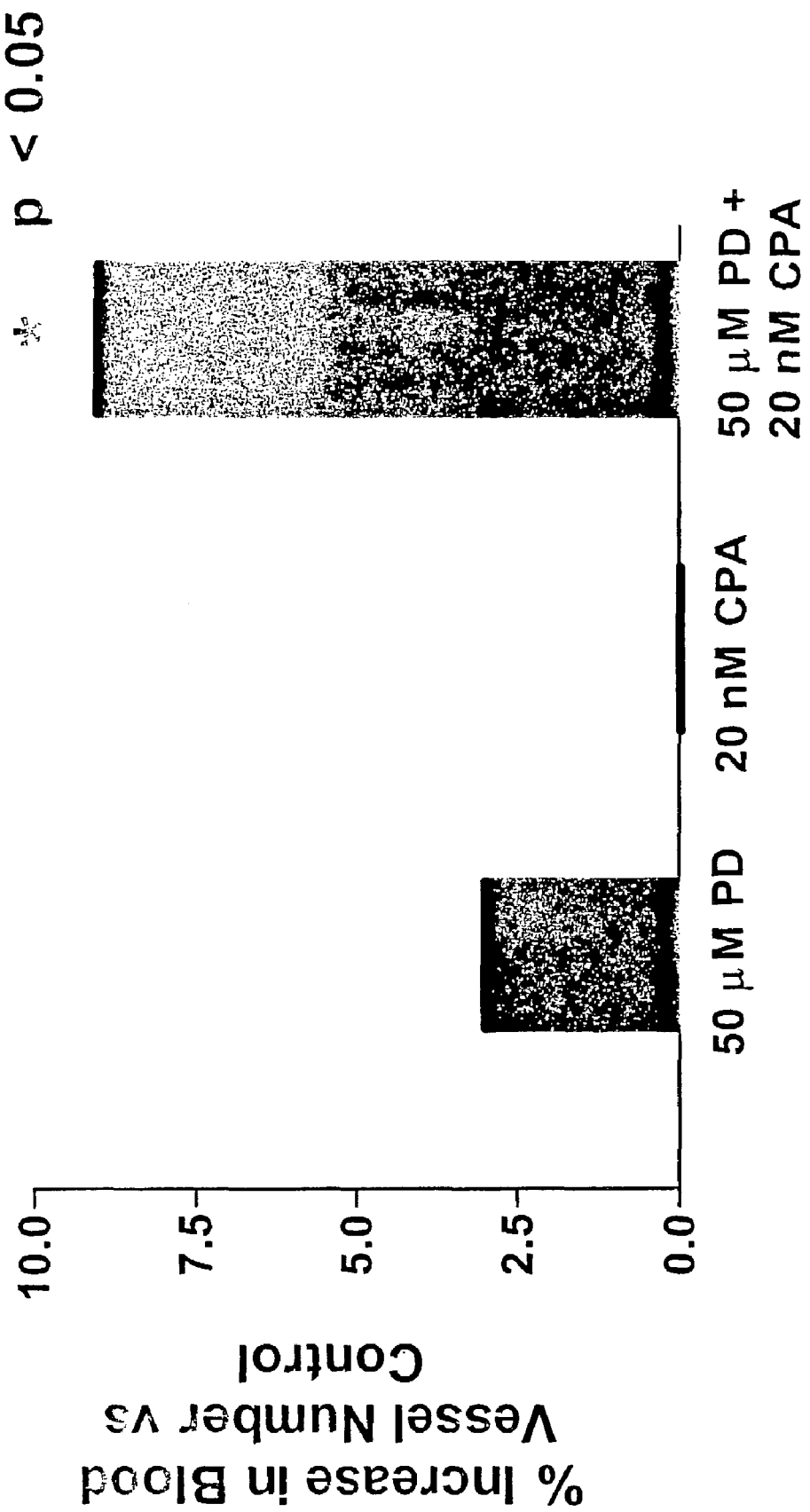
Figure 11:
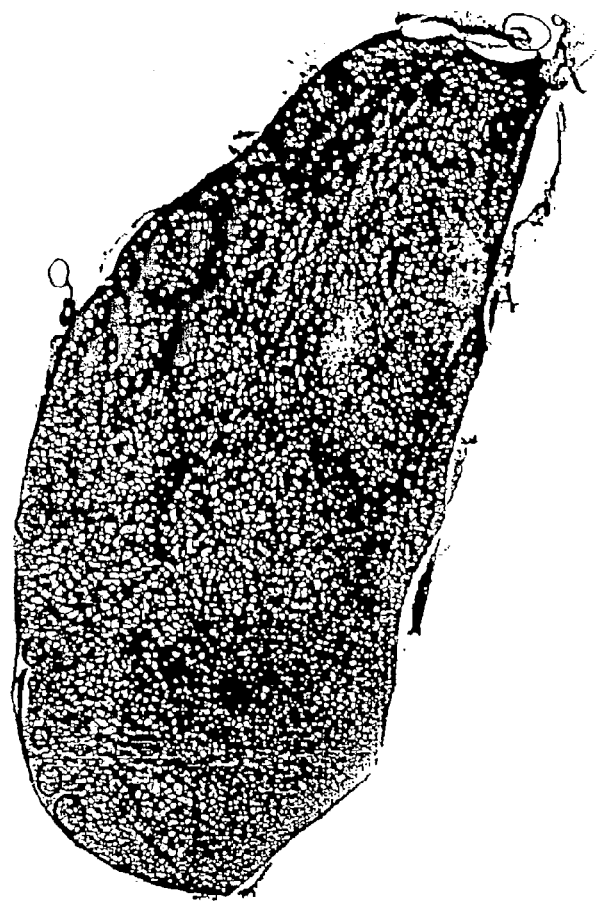
Figure 11:

FIG. 1 shows the structure of PD 81,723.
FIG. 2 shows the structure of WRC-0571.
FIG. 3 shows the structure of C17.
FIG. 4 shows the structure of ATL-MC1201.
FIG. 5 is a bar graph showing that adenosine stimulates angiogenesis in the CAM assay.
FIG. 6 is a bar graph showing that adenosine receptor subtype selective antagonists stimulate angiogenesis to varying degrees in the CAM assay.
FIG. 7 is a bar graph showing the effect of the selective adenosine $A_1$ receptor agonist cyclopentyladenosine (CPA) to stimulate angiogenesis in the chorioallantoic membrane (CAM), and the ability of the selective $A_1$ antagonist WRC-0571 to block the stimulation.
FIG. 8 is a bar graph showing stimulation of angiogenesis by PD 81,723 in the CAM. The figure also shows that WRC-0571 not only blocks the effects of PD 81,723, but of endogenous adenosine as well, suggesting that it will be a useful inhibitor of angiogenesis.
FIG. 9 is a bar graph showing the angiogenic effect of another allosteric enhancer of adenosine $A_1$ receptors, C17.
FIG. 10 is a bar graph showing the synergistic effects of PD 81,723 with CPA. In these experiments CPA was applied to CAM's at a concentration too low to cause an independent effect. PD 81,723 caused a modest effect, but when the two were combined the angiogenic effect was increased threefold over the effect seen with PD 81,723 alone.
FIG. 11 shows one of the best examples of the angiogenic effects of PD 81,723 in the rat mesentery. The control section is on the left, PD 81,723—treated on the right.

DETAILED DESCRIPTION OF THE PREFERRED EMBODIMENT

When used in pharmaceutical preparations, the compounds of this invention may be useful in the form of the free base, in the form of salts and as a hydrate. All forms are within the scope of the invention. Acid addition salts may be formed and are simply a more convenient form for use; in practice, use of the salt form inherently amounts to use of the base form. The acids which can be used to prepare the acid addition salts include preferably those which produce, when combined with the free base, pharmaceutically acceptable salts, that is, salts whose anions are non-toxic to the animal organism in pharmaceutical doses of the salts, so that the beneficial properties inherent in the free base are not vitiated by side effects ascribable to the anions. Although pharmaceutically acceptable salts of said basic compound are preferred, all acid addition salts are useful as sources of the free base form even if the particular salt per se is desired only as an intermediate product as, for example, when the salt is formed only for purposes of purification and identification, or when it is used as an intermediate in preparing a pharmaceutically acceptable salt by ion exchange procedures.

Pharmaceutically acceptable salts within the scope of the invention include those derived from the following acids: mineral acids such as hydrochloric acid, sulfuric acid, phosphoric acid and sulfamic acid; and organic acids such as acetic acid, citric acid, lactic acid, tartaric acid, malonic acid, methanesulfonic acid, ethanesulfonic acid, benzenesulfonic acid, p-toluenesulfonic acid, cyclohexylsulfamic acid, quinic acid, and the like.

The corresponding acid addition salts comprise the following: hydrochloride, sulfate, phosphate, sulfamate, acetate, citrate, lactate, tartarate, methanesulfonate, ethanesulfonate, benzenesulfonate, p-toluenesulfonate, cyclohexylsulfamate and quinate, respectively.

The acid addition salts of the compounds of this invention are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

The compounds of the present invention can be administered to a mammalian subject in a variety of forms adapted to the chosen route of administration, i.e., orally, or parenterally. Parenteral administration is preferred, and in this respect includes administration by the following routes: intravenous, intramuscular, subcutaneous, intraocular, intrasynovial, transepithelial including transdermal, ophthalmic, sublingual and buccal; topically including ophthalmic, dermal, ocular, rectal and nasal inhalation via insufflation and aerosol and rectal systemic.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparations generally contain at least 0.1% of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

Preferably, the active compound is administered parenterally or intraperitoneally. Solutions of the active compound as a free base or pharmacologically acceptable salt can be prepared in sterile water suitably mixed with a surfactant such as hydroxypropylcellulose. Dispersion can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the for must be sterile and must be fluid to the extent that easy syringability exists. It may be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by use of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yield a powder of the active ingredient plus any additional desired ingredient from previously sterile-filtered solution thereof.

The therapeutic compounds of this invention may be administered to a mammalian subject alone or in combination with pharmaceutically acceptable carriers, as noted above, the proportion of which is determined by the solubility and chemical nature of the compound, chosen route of administration and standard pharmaceutical practice.

The dosage of the present therapeutic agents which will be most suitable for prophylaxis or treatment will vary with the form of administration, the particular compound chosen and the physiological characteristics of the particular patient under treatment. Generally, small dosages will be used initially and if necessary, will be increased by small increments until the optimum effect under the circumstances is reached.

Adenosine stimulates angiogenesis in the CAM assay. Work done in the CAM by previous investigators has yielded conflicting results with respect to adenosine as a stimulator of angiogenesis. Our initial step was to see if adenosine would stimulate angiogenesis in the windowed CAM model.

EXAMPLE 1

Fertile White Leghorn chicken eggs were obtained from Truslow Farms (Chesterfield, Mo.). Eggs were incubated at 37° for 7 days, then a 1.5 cm window was cut into each egg over the CAM. Pellets were applied to the CAMs and the windows closed with cellophane tape. Eggs were incubated until day 14 when the CAMs were fixed. Adenosine was applied to the CAM via Elvdx pellets as described by Dusseau (Dusseau et al., *Stimulation of Angiogenesis by Adenosine on the Chick Chorioallantoic Membrane, Circ. Res.*, 59, 163-170, 1986). Each pellet had a 10 ul volume and contained 3 mg adenosine powder. Control pellets did not contain adenosine powder, only the Elvax polymer. The pellets were placed on the CAM where there were a few vessels present and were left in place for seven days. The CAMs then were fixed in 10% buffered formalin and vessels were counted under 20× magnification using a Nikon stereomicroscope. The quantitation of vascular number is presented as vascular density index VDI that was an adaptation of a method described by Harris-Hooker (Harris-Hooker et al., *Neovascular Responses Induced by Cultured Aortic Endothelial Cells, J. Cell. Phys.*, 114, 302-310, 1983). A plastic cover slip inscribed with 4, 5, 6, and 8 mm diameter concentric circles was centered over the adenosine pellet on the formalin-fixed CAM. The vascular density was judged by counting the numbers of the vessels which intersected the circles. This technique allowed counting of vessels down to 10-12 u in diameter. The positioning of the pellets on the CAM was randomized. From these experiments it can be seen that adenosine stimulated angiogenesis in the CAM model (see FIG. 5). The Elvax pellets themselves elicited no angiogenic responses. Adenosine was delivered by other means as well. FIG. 5 represents data from 12-15 eggs per group, showing that adenosine stimulated angiogenesis in the CAM assay.

Adenosine receptor subtype selective agonists stimulate angiogenesis to varying degrees in the CAM. FIG. 6 shows the results obtained following the application of various adenosine ligands to the CAM. In these studies, sterile filter paper disks were used to apply drug or vehicle to the CAM of eggs windowed after 7 days of incubation. The circular disk was 7 mm diameter. The agonist and antagonist drugs were delivered daily for 7 days in a volume of 100 μl placed onto the disks. On day 14 the CAMs were formalin fixed. The vessel density was determined by counting the vessels that intersected with the edge of the disks. Each bar represents data from between 13 and 19 eggs, with the exception of the bar for xanthine amine congener (XAC) which represents only four eggs. The results show a positive angiogenic response to the $A_1$ agonist CPA, the nonselective agonist NECA, and the $A_3$ selective ligand m-MECA. No angiogenic response was seen to the $A_{2A}$ agonist CGS21680 or other $A_{2A}$ selective agonists that were tried (data not shown). The nonselective antagonist XAC did not inhibit baseline angiogenesis, in fact there may be slight stimulation. It is possible that some adenosine receptors may stimulate angiogenesis, while others, particularly the $A_{2A}$ receptor, may inhibit it. Hence, XAC may release some inhibition. The 100 nM doses used should have allowed some preservation of subtype selectivity for the ligands.

EXAMPLE 2

Fertile White Leghorn chicken eggs are obtained from Truslow Labs (Maryland) and incubated until day 7 post-fertilization at 37° C. The eggs were automatically rotated by the incubator. On day 7 the eggs were candled to check for viability. The eggshell surface was cleaned with betadine and 70% isopropanol. A window 1.5×1.5 cm was cut into each egg over the CAM. The window was covered with clear cellophane tape and the eggs incubated at 37° C. overnight. The following day a sterile filter paper disc was applied to the CAM for the daily delivery of drugs or vehicle in a volume of 100 μl. CAMs were fixed on day 14 and vessels counted using the aforementioned method of Harris-Hooker et al.

EXAMPLE 3

The compound designated ATL-MC1201, illustrated in FIG. 5, is one of a new class of selective adenosine $A_1$ receptor allosteric enhancers. ATL-MC1201 was assayed as described in Example 2 for its efficacy in increasing vasculature in the CAM compared to those samples treated with vehicle alone. Vehicle consisted of 0.5% DMSO. Treatment was with 10 micromolar ATL-MC1201. Fifty microliter aliquots of vehicle (0.5% DMSO) or test compound (10 uM ATL-MC1201) were applied to the filter paper disc daily from day 7 to day 13. On day 14 the membranes were harvested and the vessels emerging at greater than 45 degrees from the disc were counted and compared between controls and treatment eggs. There were five eggs in the control group and three in the treatment group. There were an average of 75 vessels in control eggs and 94 in the treatment eggs.

EXAMPLE 4

Drug application into rat mesentery using infusion pumps. Alzet osmotic pumps were filled with drug or vehicle to a volume of 200 μl. The abdominal cavities of anesthetized 150 g Sprague-Dawley rats were incised and pumps implanted into the intraperitoneal cavity. The pumps delivered the drug at 1.0 μl/hr. After one week mesenteric samples were taken between vascular arcades along the length of the small bowel. Specimens were fixed and stained using a BS:lectin stain.

Angiogenesis stimulated by the $A_1$ agonist, CPA, was blocked by the A1-selective blocker WRC-0571, as shown in FIG. 7.

CPA at 100 nM with or without 1 μM WRC-0571 was applied to filter paper discs on developing CAMs as described above. The angiogenic effect of the drug was completely blocked by the addition of the antagonist.

Allosteric enhancers of adenosine $A_1$ receptors stimulated angiogenesis. FIG. 8 demonstrates the effect of delivering PD to the CAM. Here, PD enhances the effects of endogenous adenosine on the chicken $A_1$ receptor in the CAM. PD at a concentration of 100 μM, or vehicle, was delivered to the CAM on a filter paper disc using a protocol identical to that used for adenosine agonists. The data show that PD stimulated angiogenesis by 10%. A small effect such as this in the absence of applied ligand or ischemia/hypoxia (which would increase the endogenous adenosine levels) is expected. Because it is a rapidly growing tissue, the CAM probably has higher levels of adenosine than more quiescent tissues, resulting in a measurable effect. The effects of PD were completely blocked by WRC-0571 which also blocked the effects of endogenous adenosine as well, suggesting its usefulness as an inhibitor of angiogenesis. FIG. 9 shows that the enhancer effect is a property of the family of compounds to which PD 81,723 belongs, not specific to PD 81,723 itself. The graph shows that C17, another allosteric enhancer, also stimulates angiogenesis and is blocked by VWRC-0571.

There is synergism between agonist and PD 81,723 as shown in FIG. 10. A concentration of 20 nM CPA did not stimulate angiogenesis in the CAM. The combination of low dose CPA with PD 81,723 resulted in stimulation of angiogenesis that was three-fold greater than that seen with PD 81,723 alone. This experiment shows promise for using PD 81,723 to augment the effects of high tissue levels of adenosine.

Stimulation of angiogenesis by PD 81,723 is also seen in a mature mammalian animal model. FIG. 11 shows the effect of chronic infusion of PD 81,723 using Alzet pumps into the peritoneal cavity of a rat. The control mesentery is shown on the left, PD 81,723—treated on the right. The chronic infusion was an advantage because the model is not an ischemic one, so steady long term administration of the PD 81,723 may help to augment the effects of lower concentrations of endogenous adenosine.

The stimulation of new blood vessel growth to ischemic tissues, including the heart, brain, and extremities could dramatically impact morbidity and mortality from atherosclerotic diseases. The data show that adenosine $A_1$ receptors may play a role in the angiogenic response in addition to their other tissue protective properties and could potentially lead to new therapeutic strategies for the treatment of ischemia. The particular appeal with the allosteric enhancers is that they do not act alone, but would be most effective in hypoxic tissues with increased levels of endogenous adenosine. This could avoid some of the potential systemic adverse effects that may be seen with other therapies. There are also some advantages in choosing a secondary, rather than a primary, angiogenic factor that have already been discussed. Blockers of $A_1$ receptors are also promising for use to inhibit neovascularization where it causes or augments pathology, or as contraceptive agents to decrease the likelihood of implantation.

In accordance with one embodiment, a method for treating stroke, heart disease, and peripheral vascular disease is provided. The method comprises the step of administering to a patient an $A_1$ allosteric enhancer in an amount effective to induce angiogenesis at a desired location. In an alternative embodiment a method for treating tumors, diabetic retinopathy, inflammatory diseases such as rheumatoid arthritis and psoriasis is provided. In this method an $A_1$ antagonist is administered to the patient in an amount effective to inhibit angiogenesis at a desired location. The administered compositions can be localized in the desired tissues by any of the standard techniques know to those skilled in the art. These include direct application to the target area, either by topical application or by injection directly into or adjacent to the target tissues, or by general administration followed by targeting to the target tissue or selective accumulation to the target tissues. The compositions of the present invention can be targeted by linking the active agents to compounds that have a selective affinity for the target tissue. For example an $A_1$ antagonist or $A_1$ agonist can be linked to a monoclonal antibody that is specific for an antigen only present in the target tissue.

All publications, patents and patent documents cited herein are incorporated by reference as though individually incorporated by reference. The invention has been described with reference to various specific and preferred embodiments and techniques. However, it should be understood that many variations and modifications may be made by those skilled in the art while remaining within the spirit and scope of the invention. It will be understood that each of the elements described above, or two or more together, may also find a useful application in other types of applications differing from the type described above. This includes, for example, veterinary applications as well as the medical applications described herein.

Without further analysis, the foregoing will so fully reveal the gist of the present invention that others can, by applying current knowledge, readily adapt it for various applications without omitting features that, from the standpoint of prior art, fairly constitute essential characteristics of this invention.

The invention claimed is:

1. A method of inducing angiogenesis comprising administering to a subject in need thereof an effective angiogenesis inducing amount of an adenosine $A_1$ receptor allosteric enhancer, wherein the subject in need thereof comprises a tissue site having an ischemic injury associated with increased levels of endogenous adenosine.

2. The method of claim 1, wherein said adenosine $A_1$ receptor allosteric enhancer is (2-Amino-4,5-dimethyl-thiophen-3-yl)-(3-trifluoromethyl-phenyl)-methanone.

3. The method of claim 1, wherein said adenosine $A_1$ receptor allosteric enhancer comprises an aminothiophene.

4. The method of claim 3, wherein said adenosine $A_1$ receptor allosteric enhancer is [2-Amino-5-bromo-4-(2-naphthyl)-3-thienyl](phenyl)methanone.

5. The method of claim 1, wherein said adenosine $A_1$ receptor allosteric enhancer is 7-Oxiranylmethoxy-4,5-dihydro-3H-benzo[b]oxepin-2-one.

6. The method of claim 1, wherein the ischemic injury is from at least one of stroke, heart disease or peripheral vascular disease.

7. The method of claim 1, wherein the adenosine $A_1$ receptor allosteric enhancer is mixed with a pharmaceutically acceptable carrier.

8. The method of claim 7, wherein the carrier is suitable for one of oral, parenteral, or intraperitoneal administration.

9. A composition for inducing angiogenesis comprising an effective angiogenesis inducing amount of an adenosine $A_1$ receptor allosteric enhancer and a pharmaceutically acceptable carrier, wherein the adenosine $A_1$ receptor allosteric enhancer is 7-Oxiranylmethoxy-4,5-dihydro-3H-benzo[b]oxepin-2-one.

10. The composition of claim 9, wherein the carrier is suitable for parenteral administration to increase angiogenesis in an individual who has an ischemic injury from at least one of heart disease, stroke or peripheral vascular disease.

11. The composition of claim 9, wherein the carrier is suitable for oral administration.

12. The composition of claim 9, wherein the carrier is suitable for intraperitoneal administration.

13. A method of inducing angiogenesis comprising administering to a subject in need thereof an effective angiogenesis inducing amount of an adenosine $A_1$ receptor allosteric enhancer, wherein said adenosine $A_1$ receptor allosteric enhancer is [2-Amino-5-bromo-4-(2-naphthyl)-3-thienyl](phenyl)methanone.

14. A composition for inducing angiogenesis comprising an effective angiogenesis inducing amount of an adenosine $A_1$ receptor allosteric enhancer and a pharmaceutically acceptable carrier, wherein said adenosine $A_1$ receptor allosteric enhancer is [2-Amino-5-bromo-4-(2-naphthyl)-3-thienyl](phenyl)methanone.

15. The composition of claim 14, wherein the carrier is suitable for oral administration.

16. The composition of claim 14, wherein the carrier is suitable for intraperitoneal administration.

17. The composition of claim 14, wherein the carrier is suitable for parenteral administration.

18. A method of inducing angiogenesis comprising administering to a subject in need thereof an effective angiogenesis inducing amount of an adenosine $A_1$ receptor allosteric enhancer, wherein said adenosine $A_1$ receptor allosteric enhancer is 7-Oxiranylmethoxy-4,5-dihydro-3H-benzo[b]oxepin-2-one.

* * * * *